United States Patent
Nilsson et al.

(10) Patent No.: US 11,850,209 B2
(45) Date of Patent: Dec. 26, 2023

(54) DRIVING CONTROL OF A RECIPROCATING CPR APPARATUS

(71) Applicant: Physio-Control, Inc., Redmond, WA (US)

(72) Inventors: Anders Nilsson, Akarp (SE); Peter Sebelius, Malmo (SE)

(73) Assignee: PHYSIO-CONTROL, INC., Redmond, WA (US)

( * ) Notice: Subject to any disclaimer, the term of this patent is extended or adjusted under 35 U.S.C. 154(b) by 597 days.

(21) Appl. No.: 17/085,026

(22) Filed: Oct. 30, 2020

(65) Prior Publication Data

US 2021/0045969 A1 Feb. 18, 2021

Related U.S. Application Data

(60) Continuation of application No. 15/842,638, filed on Dec. 14, 2017, now Pat. No. 10,821,051, which is a
(Continued)

(30) Foreign Application Priority Data

Jan. 18, 2007 (SE) .................................... 0700094-6

(51) Int. Cl.
*A61H 31/00* (2006.01)
*A61M 16/00* (2006.01)

(52) U.S. Cl.
CPC ... *A61H 31/006* (2013.01); *A61H 2201/1246* (2013.01); *A61H 2201/1664* (2013.01);
(Continued)

(58) Field of Classification Search
CPC .... A61H 31/00; A61H 31/004; A61H 31/005; A61H 31/006
See application file for complete search history.

(56) References Cited

U.S. PATENT DOCUMENTS

| | | | |
|---|---|---|---|
| 3,209,747 A | 10/1965 | Guentner | |
| 3,277,887 A | 10/1966 | Thomas | |
| (Continued) | | | |

FOREIGN PATENT DOCUMENTS

WO 02091905 A2 11/2002

OTHER PUBLICATIONS

International Search Report, dated Jun. 9, 2008, 4 pages, PCT/SE2008/000022, Swedish Patent Office, Stockholm SE.
(Continued)

*Primary Examiner* — Michael J Tsai
(74) *Attorney, Agent, or Firm* — MILLER NASH LLP

(57) ABSTRACT

The disclosed mechanical cardio-pulmonary resuscitation (CPR) apparatuses, systems, and devices have a plunger and a plunger displace sensor that can sense plunger displacement information during reciprocating cycles of the plunger. The disclosure CPR apparatuses, systems, and devices also have a microprocessor unit that can receive sensed plunger displacement information from the sensor and generate plunger driving instructions based on the plunger displacement information. The plunger driving instructions have one or both of a plunger driving force and a plunger amplitude for the reciprocating cycles.

18 Claims, 14 Drawing Sheets

Related U.S. Application Data continuation of application No. 13/549,164, filed on Jul. 13, 2012, now Pat. No. 9,844,487, which is a division of application No. 12/523,082, filed as application No. PCT/SE2008/000022 on Jan. 14, 2008, now abandoned.

(52) U.S. Cl.
CPC .............. *A61H 2201/5007* (2013.01); *A61H 2201/5064* (2013.01); *A61H 2201/5066* (2013.01); *A61H 2201/5092* (2013.01); *A61M 16/00* (2013.01)

(56) References Cited

U.S. PATENT DOCUMENTS

| | | | |
|---|---|---|---|
| 3,364,924 | A | 1/1968 | Barkalow |
| 3,779,672 | A | 12/1973 | Schroeder |
| 4,273,114 | A * | 6/1981 | Barkalow ............ A61H 31/005 601/106 |
| 4,343,597 | A | 8/1982 | Brown |
| 4,471,656 | A | 9/1984 | Sanders et al. |
| 4,726,366 | A | 2/1988 | Apple et al. |
| 4,905,520 | A | 3/1990 | Nehrlich et al. |
| 6,030,353 | A | 2/2000 | Van Brunt |
| 6,155,257 | A | 12/2000 | Lurie et al. |
| 6,171,267 | B1 | 1/2001 | Baldwin, II |
| 6,215,299 | B1 * | 4/2001 | Reynolds ............... G01D 5/145 324/207.2 |
| 6,397,843 | B1 | 6/2002 | Tien-Tsai |
| 6,652,039 | B1 | 11/2003 | Shull et al. |
| 6,919,719 | B2 | 7/2005 | Reininger |
| 7,118,542 | B2 | 10/2006 | Palazzolo et al. |
| 7,226,427 | B2 | 6/2007 | Steen |
| 7,517,325 | B2 | 4/2009 | Halperin |
| 8,007,451 | B2 | 8/2011 | Havardsholm et al. |
| 2002/0077752 | A1 * | 6/2002 | Burreson ............... G01D 5/251 324/207.23 |
| 2003/0181834 | A1 | 9/2003 | Sebelius et al. |
| 2004/0230140 | A1 | 11/2004 | Steen |
| 2004/0263155 | A1 | 12/2004 | Schroeder et al. |
| 2005/0058977 | A1 | 3/2005 | Cantrell et al. |
| 2006/0059995 | A1 | 3/2006 | Gustafson et al. |
| 2006/0087313 | A1 | 4/2006 | Revankar et al. |
| 2006/0094991 | A1 * | 5/2006 | Walker ............... A61H 31/006 601/41 |
| 2006/0173500 | A1 * | 8/2006 | Walker ............... A61B 5/0809 607/5 |
| 2006/0196354 | A1 | 9/2006 | Garcia et al. |
| 2007/0225623 | A1 * | 9/2007 | Freeman ........... A61M 16/1075 601/44 |
| 2007/0270724 | A1 * | 11/2007 | Havardsholm ...... A61H 31/005 601/41 |
| 2007/0276300 | A1 | 11/2007 | Olson et al. |
| 2008/0097257 | A1 * | 4/2008 | Stromsnes ............. A61H 31/00 601/41 |
| 2009/0278641 | A1 * | 11/2009 | Hedayat ............. F15B 15/2861 335/284 |
| 2011/0120300 | A1 | 5/2011 | Fletcher et al. |

OTHER PUBLICATIONS

Written Opinion, dated Jun. 9, 2008, 5 pages, PCT/SE2008/000022, Swedish Patent Office, Stockholm SE.
European Search Report for EP App. No. 13155766.2, dated May 8, 2013, 6 pages.

\* cited by examiner

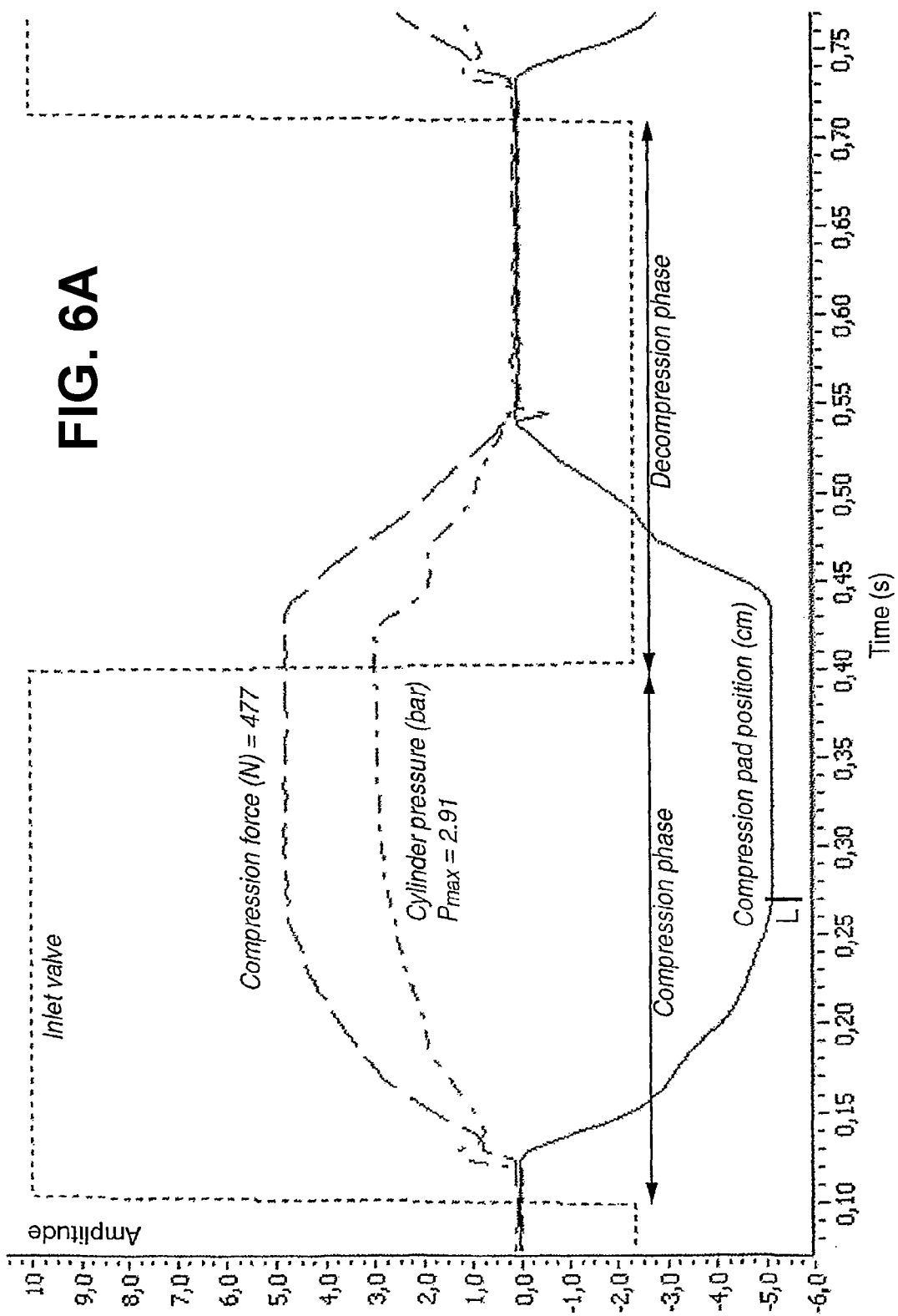

DRIVING CONTROL OF A RECIPROCATING CPR APPARATUS

RELATED APPLICATIONS

This application is a continuation of U.S. patent application Ser. No. 15/842,638, filed Dec. 14, 2017, which itself is a continuation of U.S. patent application Ser. No. 13/549,164, filed Jul. 13, 2012 and issued as U.S. Pat. No. 9,844,487 on Dec. 19, 2017, which is a division of U.S. patent application Ser. No. 12/523,082, filed Aug. 13, 2009, now abandoned, which is a national stage entry of International Patent Application No. PCT/SE2008/000022, filed Jan. 14, 2008, which claims the benefit of Swedish Application No. 0700094-6, filed Jan. 18, 2007.

BACKGROUND

In cardio-pulmonary resuscitation (CPR) repeated compressions are administered by hand or by apparatus to the chest of the person being resuscitated to maintain circulation and oxygenation of blood. Concomitant with the compressions electrical shocks can be provided to the patient to make the heart beat again. Gas-driven reciprocating CPR apparatuses have been known in the art and used in practice for a long time. Providing compressions of correct depth is an important factor for success of the method.

SUMMARY

The disclosed mechanical cardio-pulmonary resuscitation (CPR) apparatuses, systems, and devices have a plunger and a plunger displace sensor that can sense plunger displacement information during reciprocating cycles of the plunger. The disclosure CPR apparatuses, systems, and devices also have a microprocessor unit that can receive sensed plunger displacement information from the sensor and generate plunger driving instructions based on the plunger displacement information. The plunger driving instructions have one or both of a plunger driving force and a plunger amplitude for the reciprocating cycles.

BRIEF DESCRIPTION OF THE DRAWINGS

The invention will now be explained by reference to preferred but not limiting embodiments thereof illustrated in a rough drawing, in which

FIGS. 6A-6C are graphs illustrating the effect of driving gas valve opening times on gas consumption in reaching and maintaining a desired compression depth against a given resilient force in CPR model experiments;

DETAILED DESCRIPTION

Figure 1A:
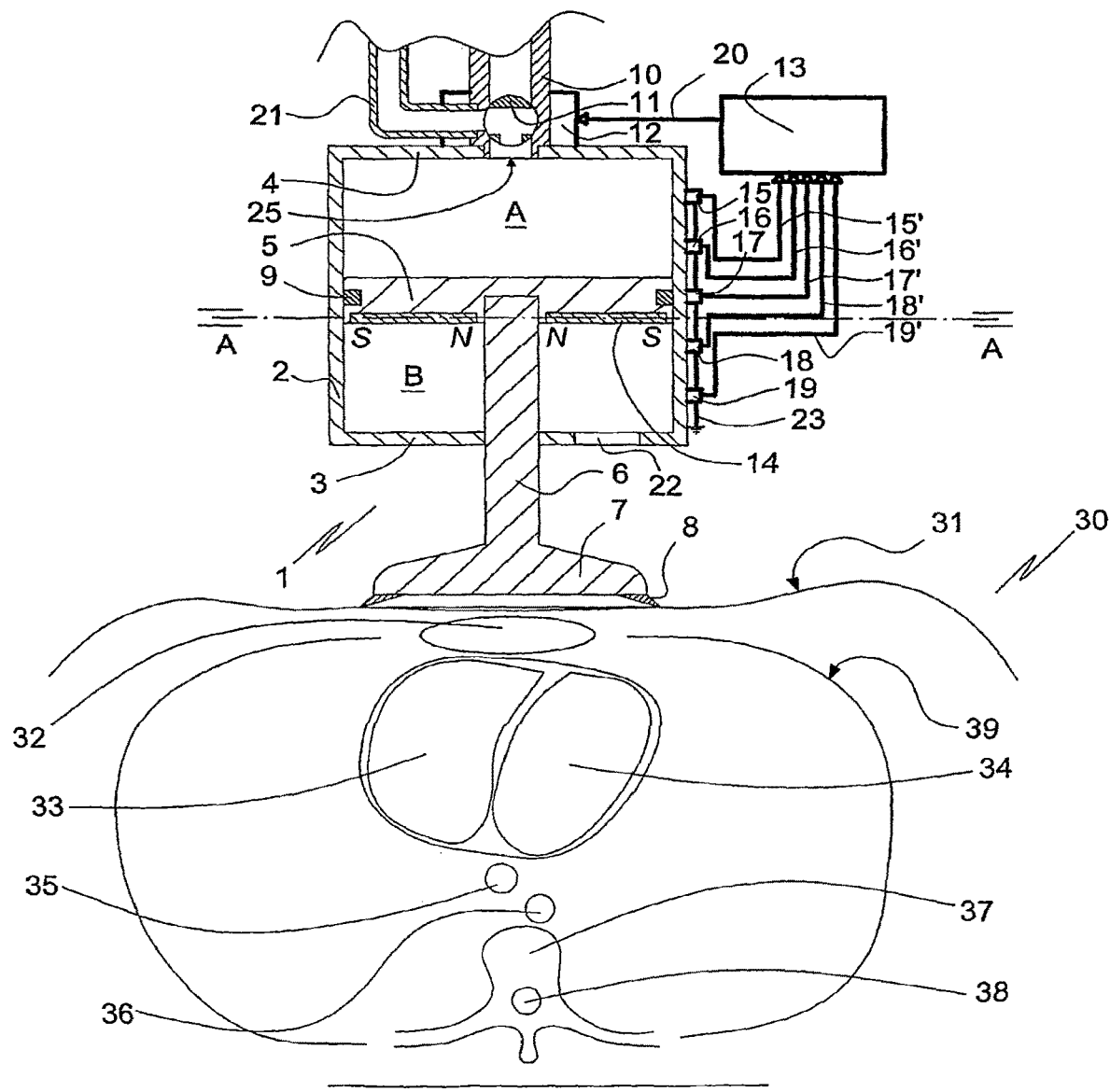
FIG. 1A is a sectional view of a first embodiment of the apparatus of the invention disposed on the chest of a patient shown in a transverse section at the level of the eight thoracic vertebra (T8) and viewed in a cranial direction.
Figure 1B:
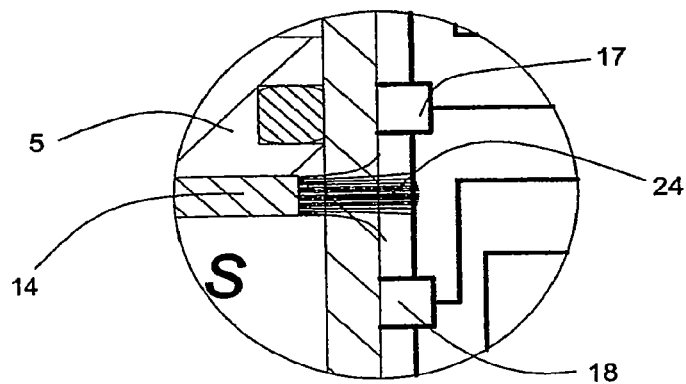
FIG. 1B is a detail view of the embodiment of FIG. 1A, in the same view and enlarged.

In the following, "Compression Depth" signifies the maximum sternal deflection during a compression/decompression cycle. An appropriate Compression Depth for adult persons corresponds to a sternal deflection of 20%; the compression depth for a chest with an anterior-posterior diameter of 25 cm thus is 5 cm. In contrast "compression depth" in the following refers to a sternal deflection during a compression/decompression cycle smaller than the maximum deflection or to sternal deflection in general.

Shallow compressions may be insufficient to restore circulation and oxygenation while compressions that are too deep may damage the ribs and the soft tissues of the chest. There is thus an optimal Compression Depth or a narrow range of optimal Compression Depths. Administration of compressions of optimal Compression Depth may be controlled by administering compressions of a given force. Alternatively, a desired Compression Depth may be set by an operator; it may be optionally changed during resuscitation. Alternatively, the Compression Depth in a CPR apparatus can be set by limiting the stroke of the piston in the apparatus to the average optimal Compression Depth for an adult person. A given compression force results in a compression to a Compression Depth at which the compression force is balanced by the resistive force of the chest tissues. Since even adult persons differ in their chest anatomy a given compression force may result in compression of varying depth in a group of persons. Therefore the direct determination of Compression Depth during cardiopulmonary resuscitation and its use for control of the apparatus by which the compressions are administered is desirable.

The determination of compression depths during cardio-pulmonary resuscitation is known in the art. An accelerometer-based compression monitor is placed on the patient's sternum, the arm of a rescuer administrating manual heart compressions or on a compression-administrating part of an automatic CPR device. The chest is then compressed. The accelerometer signal is integrated and fed to a processor, which calculates the compression depth from the signal by use of complex algorithms. The accelerometer is electrically connected to the processor.

In the administration of repeated compressions in cardio-pulmonary resuscitation, the use of apparatus based on a reciprocating piston provided with a chest compression pad and mounted in a cylinder is known. The piston is driven by a compressed gas. The Compression Depth administered with such an apparatus is limited by physical means comprised by the apparatus and set from start to from about 40 mm to about 50 mm for an adult person.

The embodiment of the apparatus 1 of the invention shown in FIGS. 1A-2H comprises a cylinder housing of a diamagnetic material having a side wall 2, a bottom 3 and a top wall 4. A piston 5 with a circumferential sealing 9 is mounted in the housing and defines an upper compartment A and a lower compartment B. A plunger 6 extends downwards from the center of the piston 5, passing through a central bore in the bottom 3 of the housing. At its free end the plunger 6 carries a chest compression pad 7 provided with a flexible circumferential lip 8. The piston 5/plunger 6/compression pad 7 is mounted displaceably in the cylinder housing. A neodymium magnet ring 14 is mounted at the lower face of the piston 5 with its south pole S facing the side wall 2. An array of unipolar Hall-Effect digital switches ("unipolar Hall switches") 15, 16, 17, 18, 19 is mounted at the outer wall of the cylinder 1 in an axial direction. The unipolar Hall switches 15, 16, 17, 18, 19 are characterized by their magnetic operating threshold. If the Hall cell of a switch 15, 16, 17, 18, 19 is exposed to the magnetic field of the south pole exceeding the operating threshold, the output transistor is switched on. If the field drops below the switching threshold, the transistor is switched off. One pole of each of the unipolar Hall switches 15, 16, 17, 18, 19 is grounded at 23 whereas the other is fed with 3 V DC by lines 15', 16', 17', 18', 19', respectively, connected to a microprocessor unit 13. In FIG. 1B the field lines 24 of the magnet's 14 south pole S are shown in respect of unipolar Hall switches 18, 19 to illustrate how the latter are influenced during a displacement of the plunger 6. The effect (Hall effect) by which the switches 15, 16, 17, 18, 19 are closed by the influence of the field of the magnet 14 allows to monitor the passage of the plunger by the microprocessor unit 13 (FIG. 3). During passage of the magnet 14 the circuit of the respective switch 15, 16, 17, 18 or 19 is closed, the current passing a closed switch being recorded by the microprocessor unit 13. After passage of the magnetic field the respective switch is again opened except for if the plunger stops in a position in which the magnetic field does cover it after stop. This allows the microprocessor unit 13 to keep track of the movement of the piston 5/plunger 6/pad 7 assembly and, in particular, its position at the end of its downward or, less important, upward movement, and to control the provision of compressed breathing gas to compartment A by the solenoid valve based on that position.

For reasons of simplicity number of unipolar Hall switches in the embodiment of FIGS. 1A to 2H is confined to five. An embodiment that allows to obtain fine tuning of positional control can comprise a higher number of unipolar Hall switches and/or have the switches disposed in the region of the compression depth level where the determination of position of piston 5/plunger 6/compression pad 7 is most important. Other Hall-effect switches like bipolar and omnipolar Hall-effect switches may be used for sending the field of magnet 14.

Figure 1C:
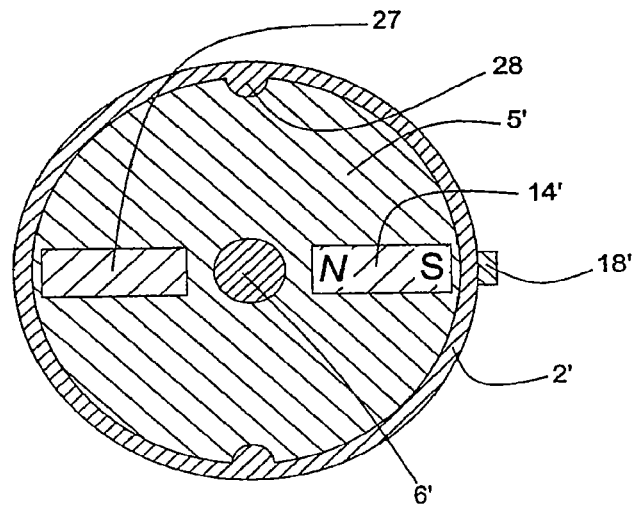
FIG. 1C is a section A-A (FIG. 1A) through a modification of the apparatus of FIG. 1A.

In a modification of the embodiment of FIG. 1A the ring magnet 14 is exchanged for a rod magnet 6' (FIG. 1C). For reasons of balance a counter weight 27 is mounted diametrically opposite to the magnet 6' at the lower face of the piston 5'. The use of a rod magnet 6' requires the arrangement of a means preventing rotation of the piston 5'. In FIG. 1C the rotation preventing means comprises two diametrically opposite axially extending flanges 28 protruding from inner face of the cylinder side wall 2' and co-operating with diametrically opposite axially extending slits in the side wall of piston 5'. Also shown is a Hall-effect switch 18' mounted at the outer face of the side wall 3' opposite to the south pole of magnet 14'.

Returning to the embodiment of FIGS. 1 and 2A-2H the upper compartment A of the housing is defined by the top face of the piston 5, a first portion of the side wall 2 of the housing, and the top wall 4 of the housing, whereas its lower compartment B is defined by the bottom face of the piston 5, the bottom face of the magnet 14, a second portion of the side wall 2 and the bottom wall 3. An opening 22 in the bottom wall 3 allows air to enter into compartment B or to be expelled from it depending on the direction of displacement of the piston 5.

Figure 1D:
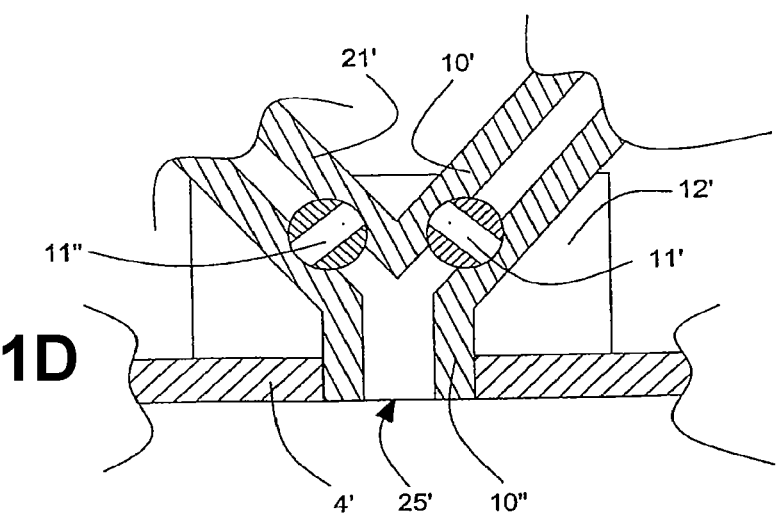
FIG. 1D is a detail view of another modification of the apparatus of FIG. 1A showing solenoid valve control unit with a pair of solenoid valves.

A tube 10 for providing compressed breathing gas from a gas supply such as a gas cylinder or other container of compressed breathing gas (not shown) is mounted at and communicates with an opening 25 in the top wall 4. Near the opening 25 a venting tube 21 branches off from tube 10. Tube 21 can be put in communication with a breathing mask (not shown) borne by the patient under cardiopulmonary resuscitation. A three-way solenoid valve 11 controlled by a solenoid control unit 12 is mounted in the lumen of tube 10 at the branching of the venting tube 21. In a first position P1 the solenoid valve 11 allows compressed breathing gas to enter compartment A through opening 25. In a second position P2 the solenoid valve 11 allows to vent compressed air in compartment A through venting tube 22. The solenoid valve 11 is only shown schematically in the Figures; its design allows switching between positions P1 and P2 without passing an intermediate position in which the lumina of tubes 10 and 21 and the compartment A are in simultaneous communication. The solenoid valve is actuated by a solenoid valve control unit 12 receiving actuation signals from the microprocessor unit 13 via line 20. The microprocessor unit 13 and the solenoid valve control unit 12 are energized by a dry battery (not shown). The three-way solenoid valve 11 of the embodiment of FIGS. 1 and 2A to 2H can be exchanged for a pair of solenoid valves 11', 11" actuated by a solenoid valve control unit 12' (FIG. 1D). Reference numbers 4', 10', 21' and 25' identify elements corresponding to elements 4, 10, 21 and 25, respectively, of the embodiment of FIGS. 1 to 2H.

After leaving the gas cylinder the compressed breathing gas is decompressed in controlled manner (not shown) to a working pressure, which is kept about constant during CPR. The gas of working pressure is suitable held in a reservoir from which the gas of working pressure is adduced to the compartment A via tube 10 so as to provide it at an about constant gas pressure over time. This allows the provision of a controlled compression force via the piston 5, the plunger 6, and the pad 7 to the chest of a patient. Since the adduction of compressed gas through tube 10 and the build-up of gas pressure in compartment A is a dynamic process governed by the pressure of the gas in the gas reservoir, the gas pressure in the compartment 10 (the pressure of the "provided" driving gas) is not in equilibrium with the pressure of the driving gas at the source over an initial portion of the compression phase.

The compression pad 7 is loosely placed on the chest 30 of a person to be provided chest compressions (FIG. 1A). The person is in a recumbent position with the pad 7 placed on the skin 31 above the sternum 32. Reference numbers denote: 33, right ventricle; 34, left ventricle; 35, esophagus; 36, descending aorta; 37, body of the eight thoracic vertebra (T8); 38, spinal cord; 39 left arc of ribs.

The function of the apparatus of the invention will now be explained with reference to FIGS. 2A through 2H.

Figure 2A:
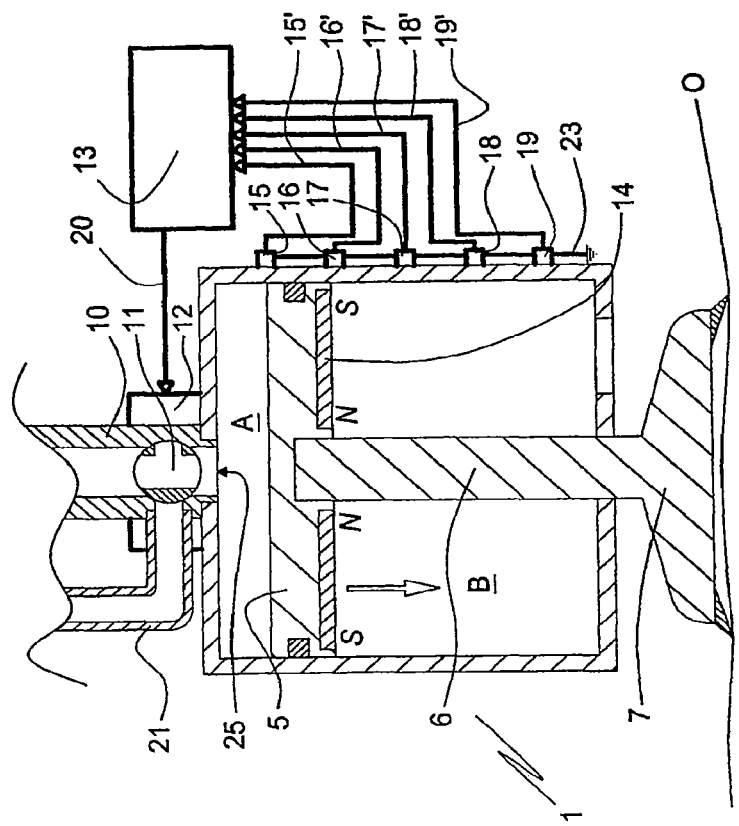
FIGS. 2A-2H show the embodiment of FIG. 1A and in the same view, in consecutive states of chest compression by reciprocating displacement of its piston and compressing pad.
Figure 2B:
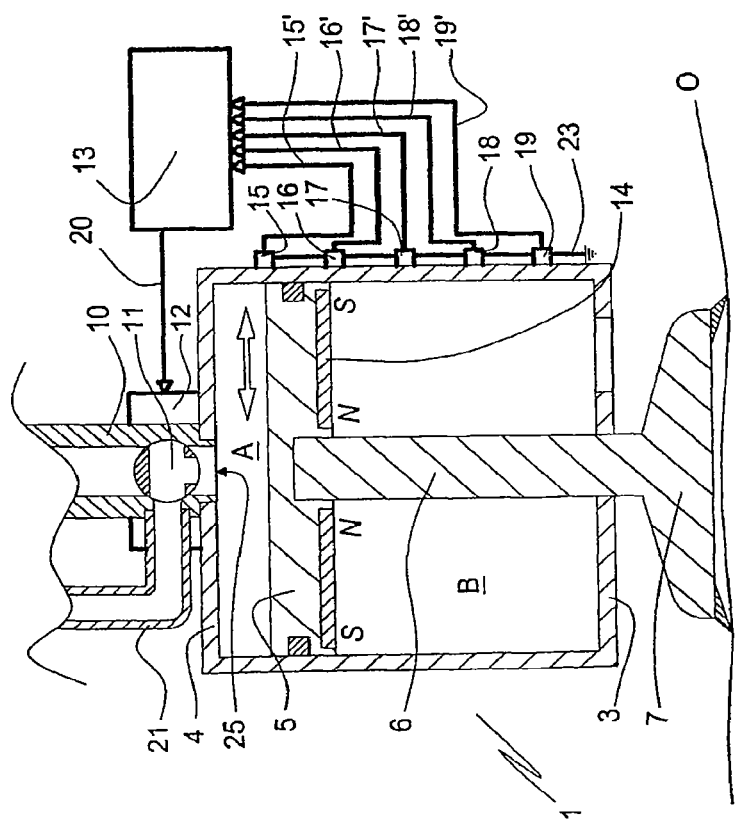
Figure 2C:
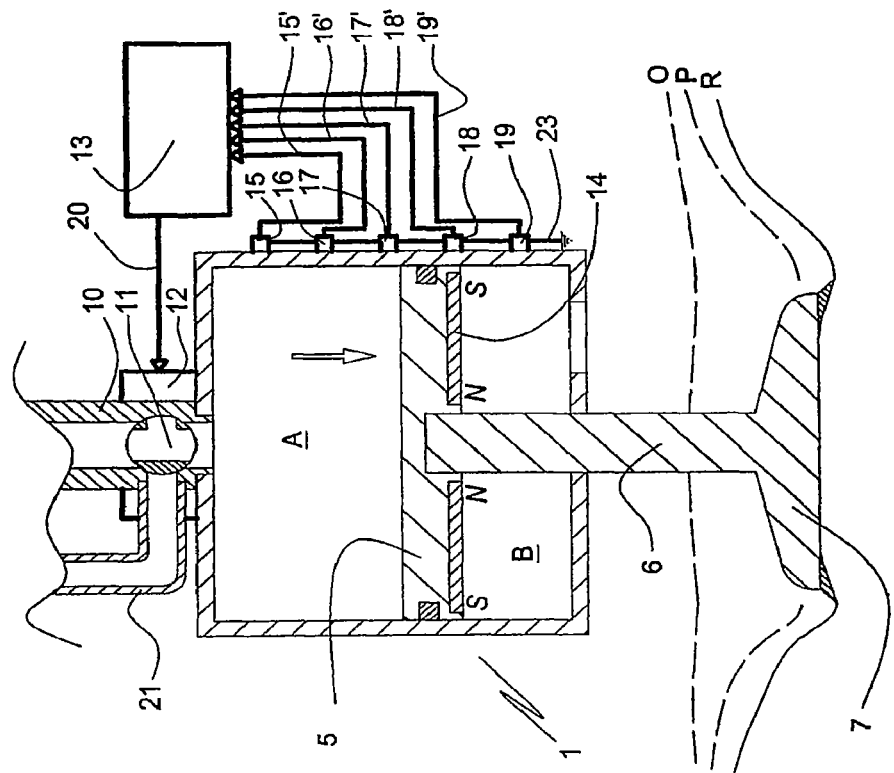
Figure 2D:
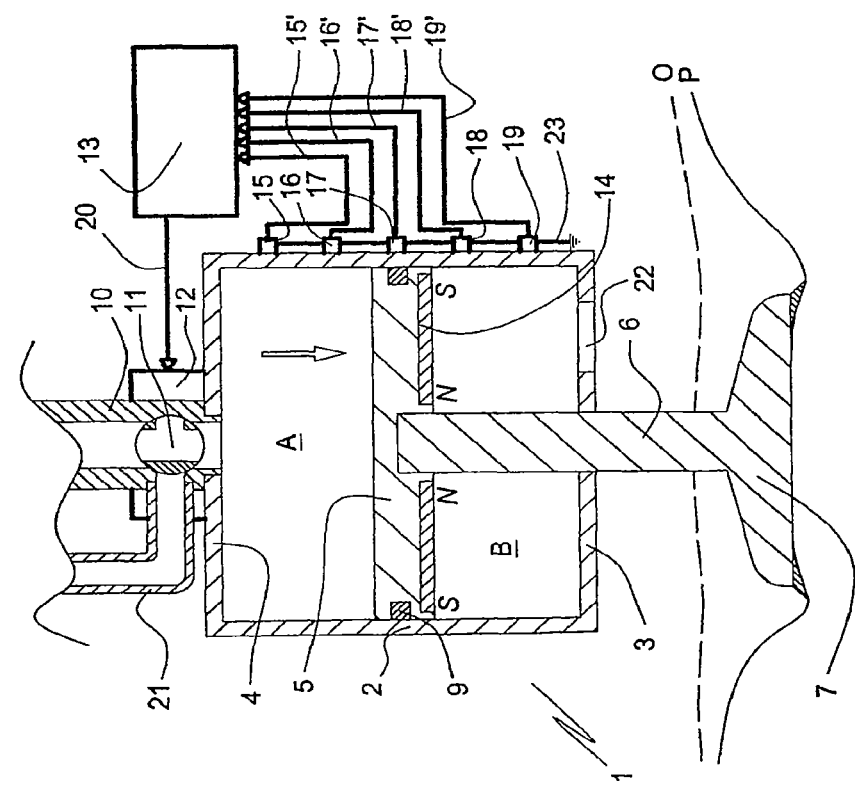
Figure 2E:
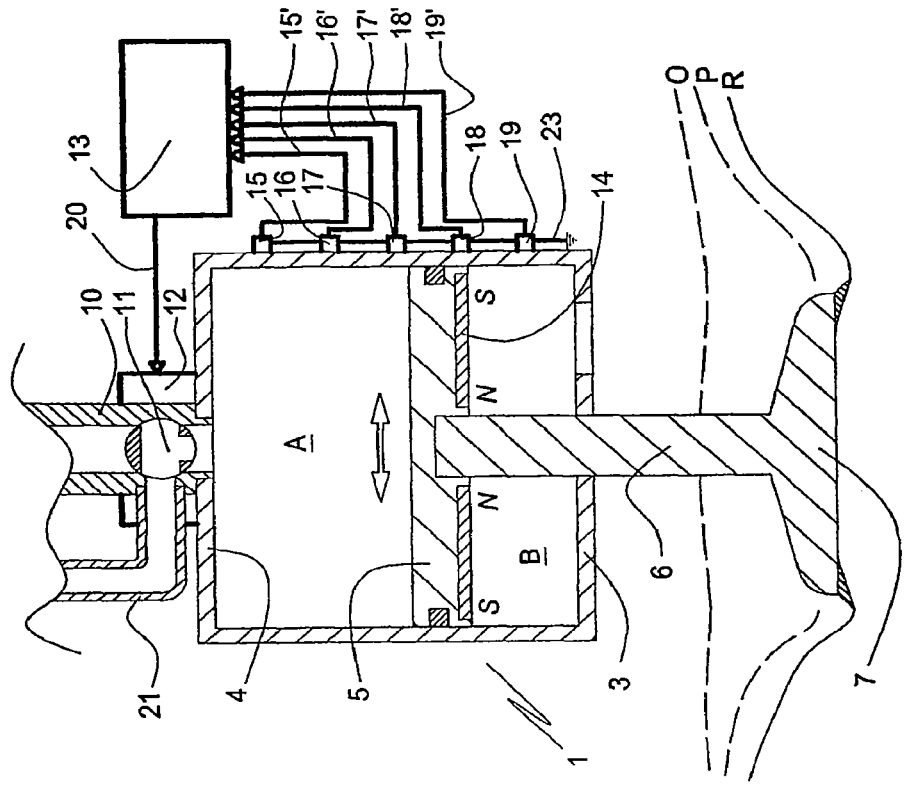
Figure 2F:
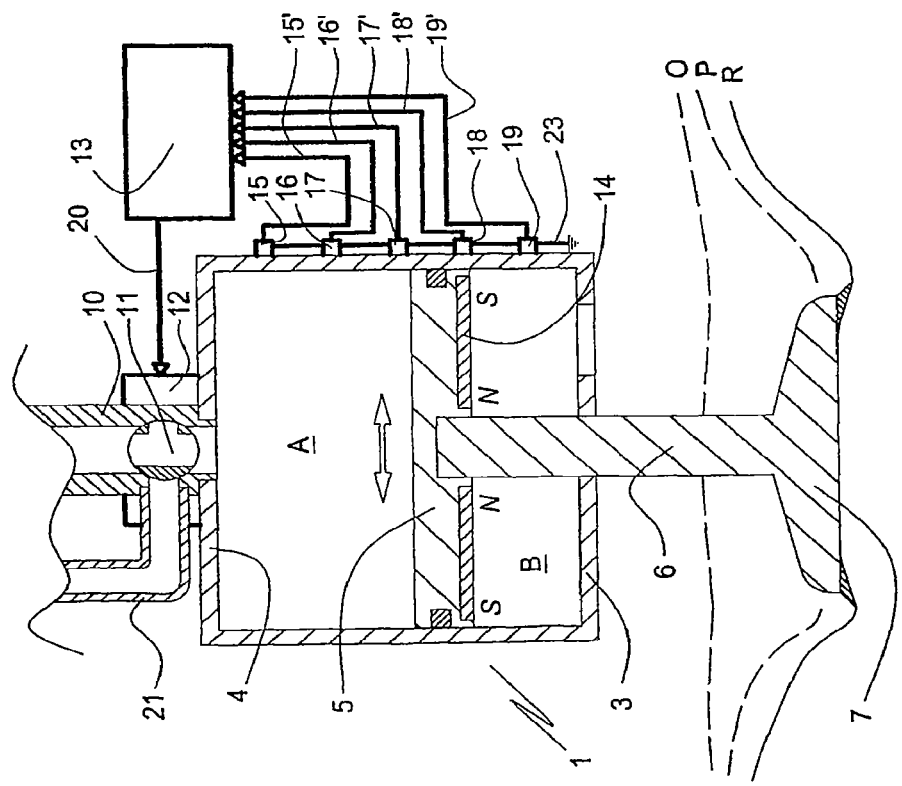

The position at the start of dispensation of chest compression is shown in FIG. 2A, which corresponds to FIG. 1A except for that only the skin 31 of the patient's chest in the sternal region is shown. In the Figures the uncompressed level of the skin 31 at the application site of the pad 7 is designated 0. The solenoid valve 11 is in the venting position P1 and the plunger is in an unloaded state. By opening of the venting valve 11 (valve position P2) compressed air is made to flow from the gas cylinder to tube 10 and to enter compartment A through opening 25. The increasing air pressure in compartment A starts to force the piston 5 downwards in the direction of bottom wall 3 (FIG. 2B; start of downward movement of piston 5 indicated by an arrow). At start the south pole S of the magnet 14 is disposed between Hall switches 15 and 16. During its downward movement (FIG. 2C; valve 11 in position P2; skin level at intermediate position P during downward movement) the south pole S of the magnet 14 passes Hall switches 16, 17 and stops at the level of switch 18 (skin level Rat initial full compression=Compression Depth in an initial cycle of CPR). It stops at because, at this level, the compression force of the compressed gas acting on the piston 5 transferred by the pad 7 to the patient is balanced by the resilient counterforce of the compressed chest tissues. As explained above, the microprocessor unit 13 keeps track of the position of the piston 5 during its downward (and upward, if desired) movement, and recognizes the exact moment at which the piston 5/plunger 6/rod 7 assembly has reached its extreme position during its downward movement (FIG. 2D, indicating the infinitesimal last downward movement of piston 5/plunger 6/rod 7 assembly prior to stop with the valve 11 in position P1; FIG. 2E, the moment of stop with the valve 11 in position P1; and, at the same moment, FIG. 2F, an immediate switch of the valve 13 from position P1 to P2. As explained above and if desired, the switch of the solenoid valve 11 from P1 to P2 can be made to occur slightly earlier, that is, prior to the piston 5/plunger 6/rod 7 assembly reaching its downward stop position by programming of the microprocessor 13 correspondingly. The recognition of the time when the piston 5/plunger 6/rod 7 assembly reaches its lower end or bottom position moment thus is used for control of the solenoid valve so as to switch it from position P2 to P1. The flow of compressed gas into compartment A is stopped at the moment where the piston 5/plunger 6/rod 7 assembly reaches the desired extreme position (Compression Depth) or slightly before that moment. Thereby the provision of driving gas is optimized and thus economized. This is of particular importance for a CPR apparatus to be used outside facilities like a hospital where practically unlimited resources of compressed gas of various kind are available. In the state of the apparatus shown in FIG. 2F compartment A is vented via tube 21. If the driving gas is a breathing gas the vented gas or a portion thereof, which is still of a slightly higher pressure than ambient air, can be adduced to the patient's lungs via a breathing mask or by intubation (not shown). The venting of compartment A stops the load on the piston 5/plunger 6/rod 7 assembly (FIG. 2G) and thus the compression of the patient's chest. The resilient nature of the chest makes it expand and push the piston 5/plunger 6/rod 7 assembly back to its start position (FIG. 2H).

The microprocessor unit 13 of the apparatus of the invention is programmed in a manner so as to sample and store positional data over one or several cycles, and to use such data for control of a later cycle.

Figure 2H:
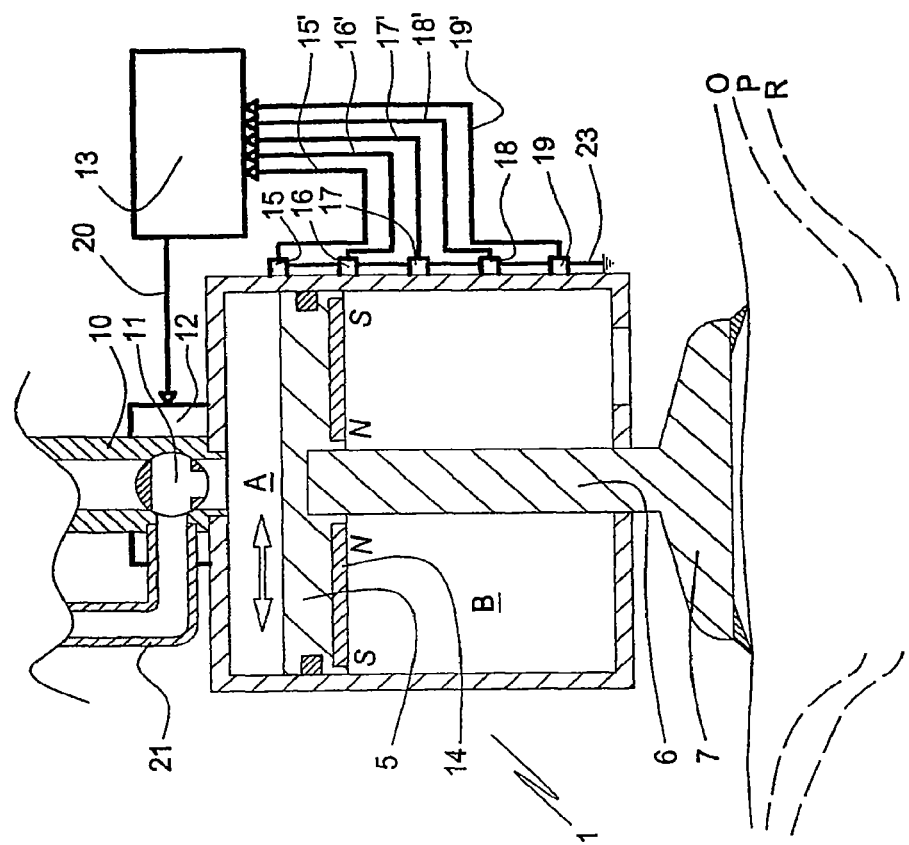
Figure 2G:
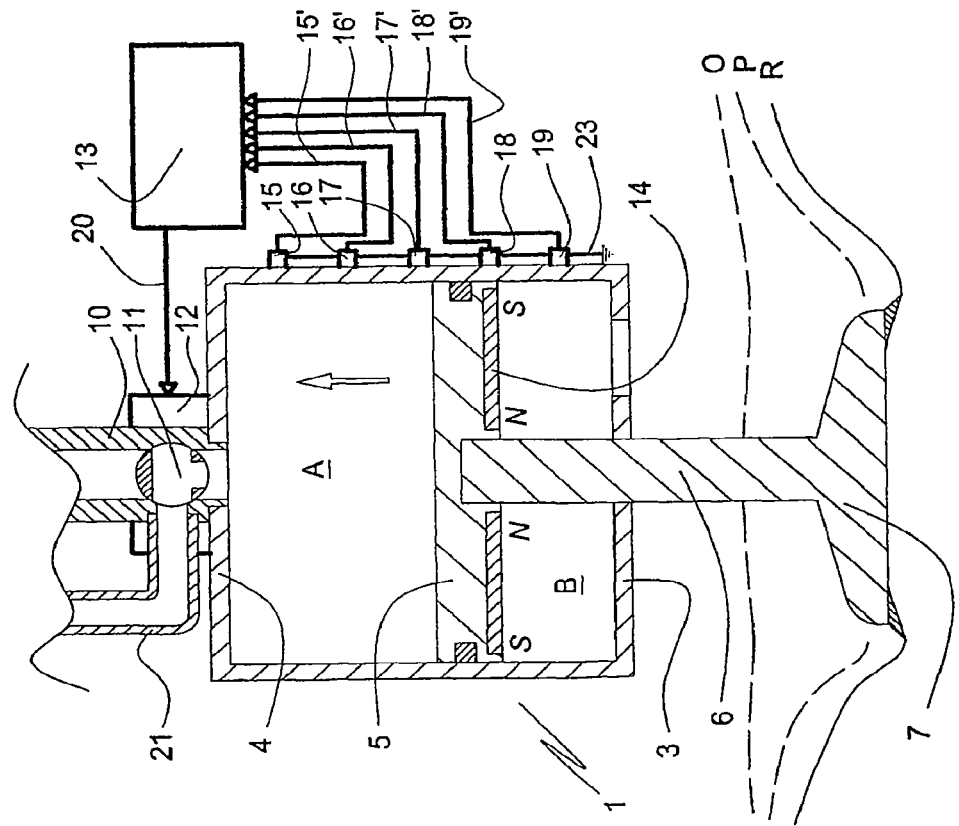
Figure 3:
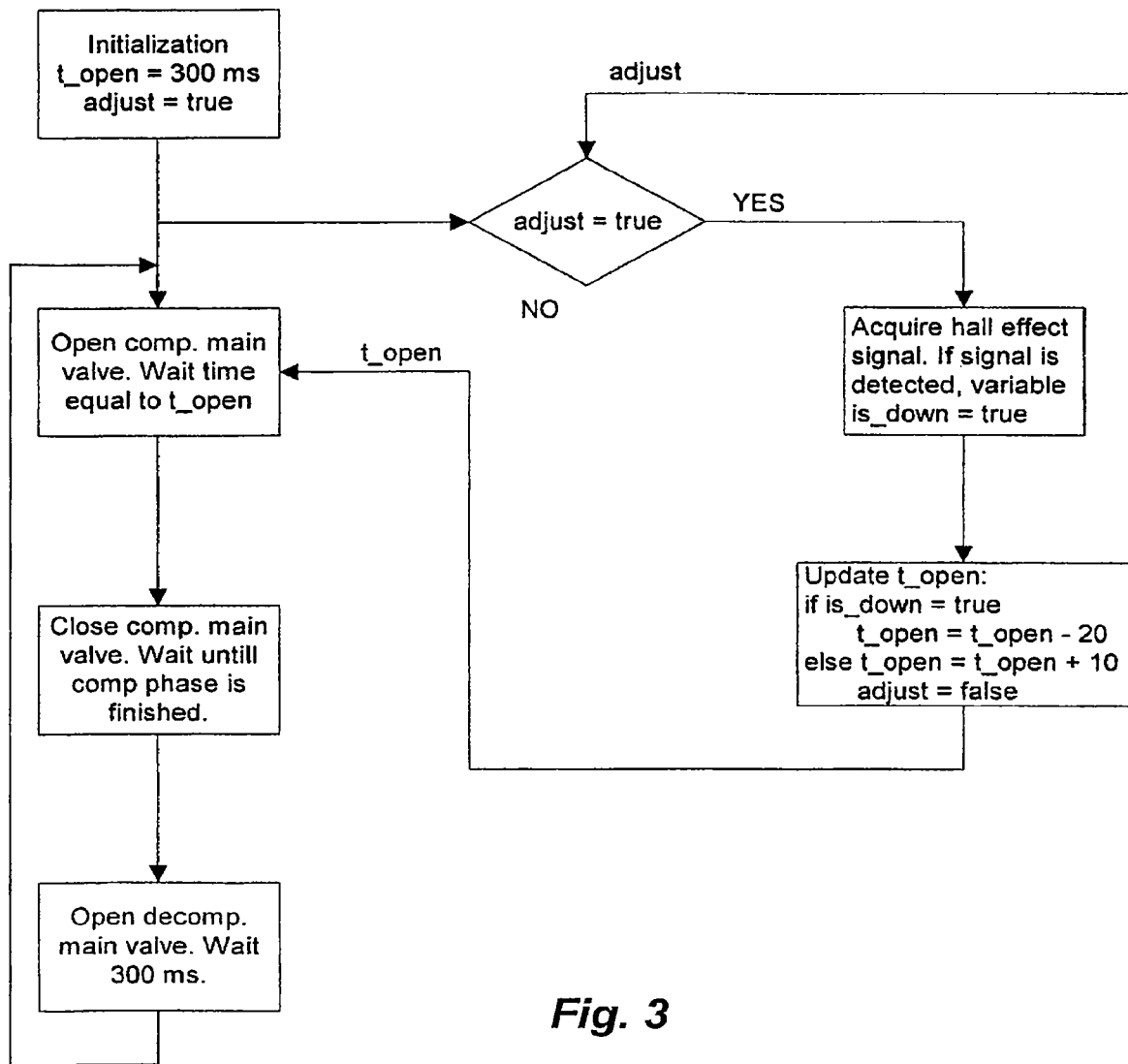
FIG. 3 is a block scheme of a solenoid valve control program.
Figure 4A:
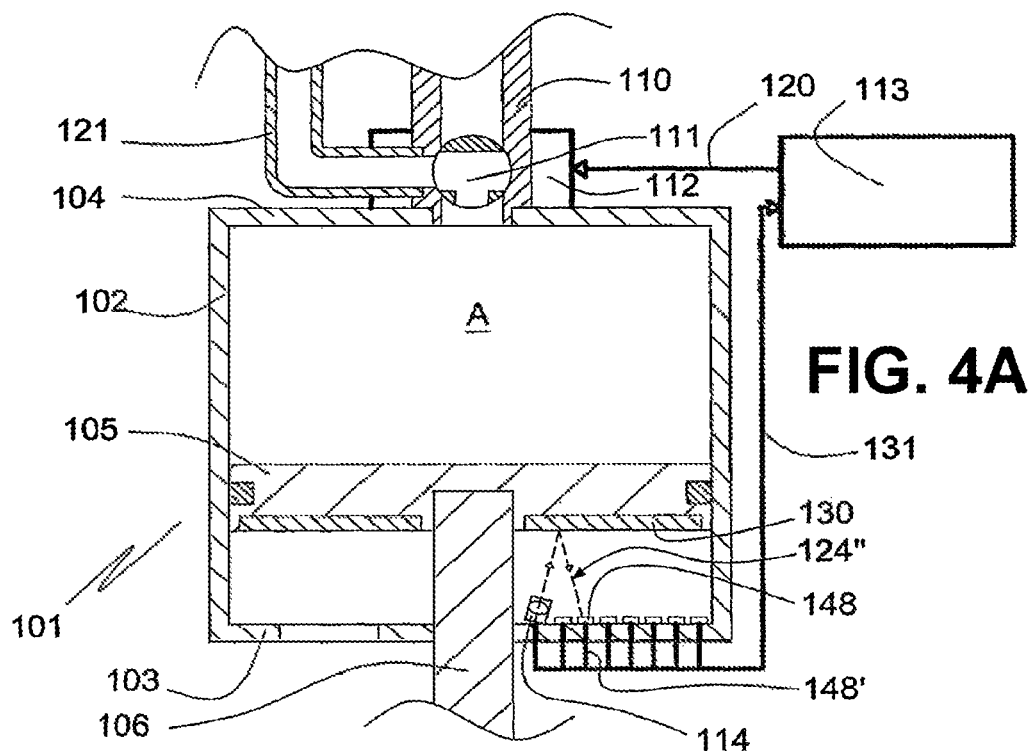
FIGS. 4A-4D show another embodiment of the apparatus of the invention, in the same view as in FIG. 1A and, in FIGS. 4D and 4D, partially enlarged.
Figure 4B:
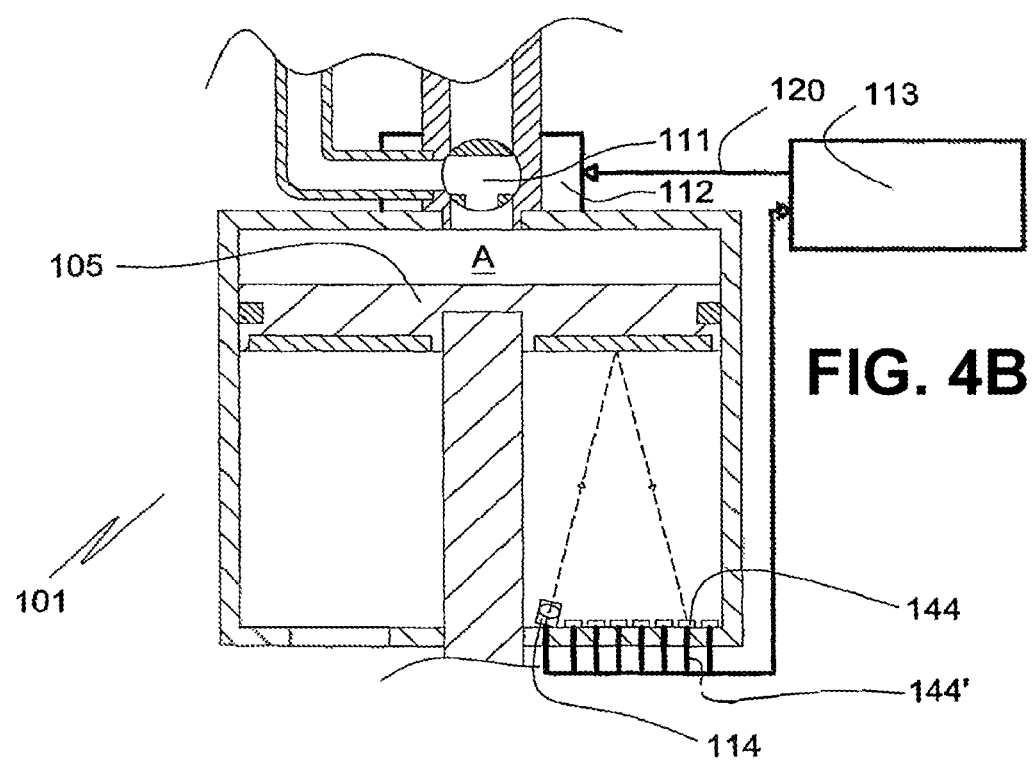
Figure 4C:
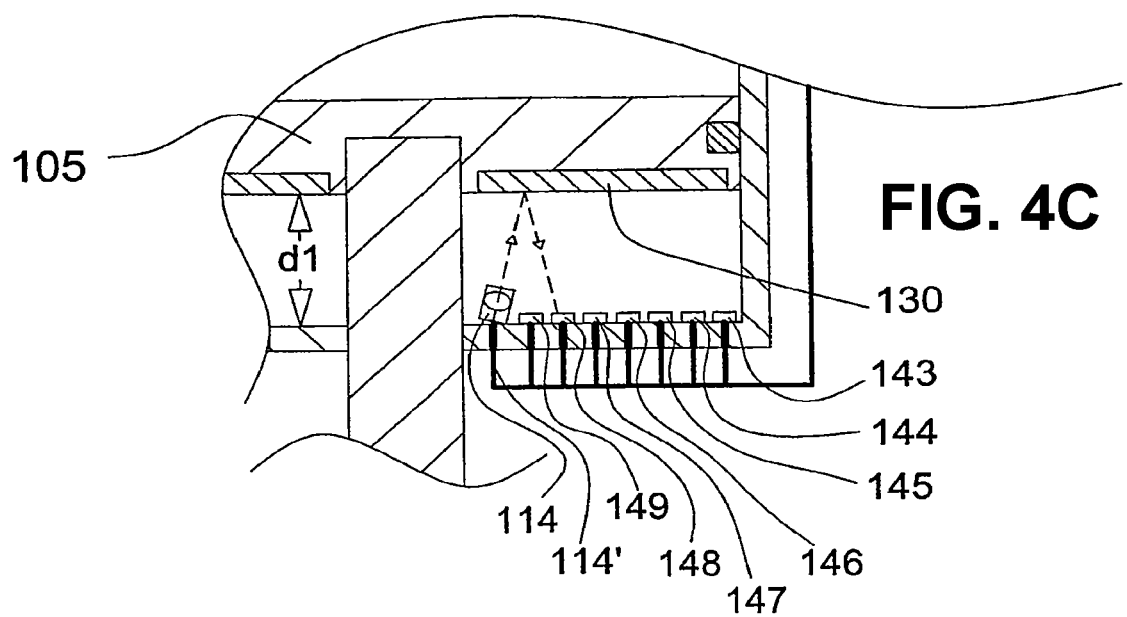
Figure 4D:
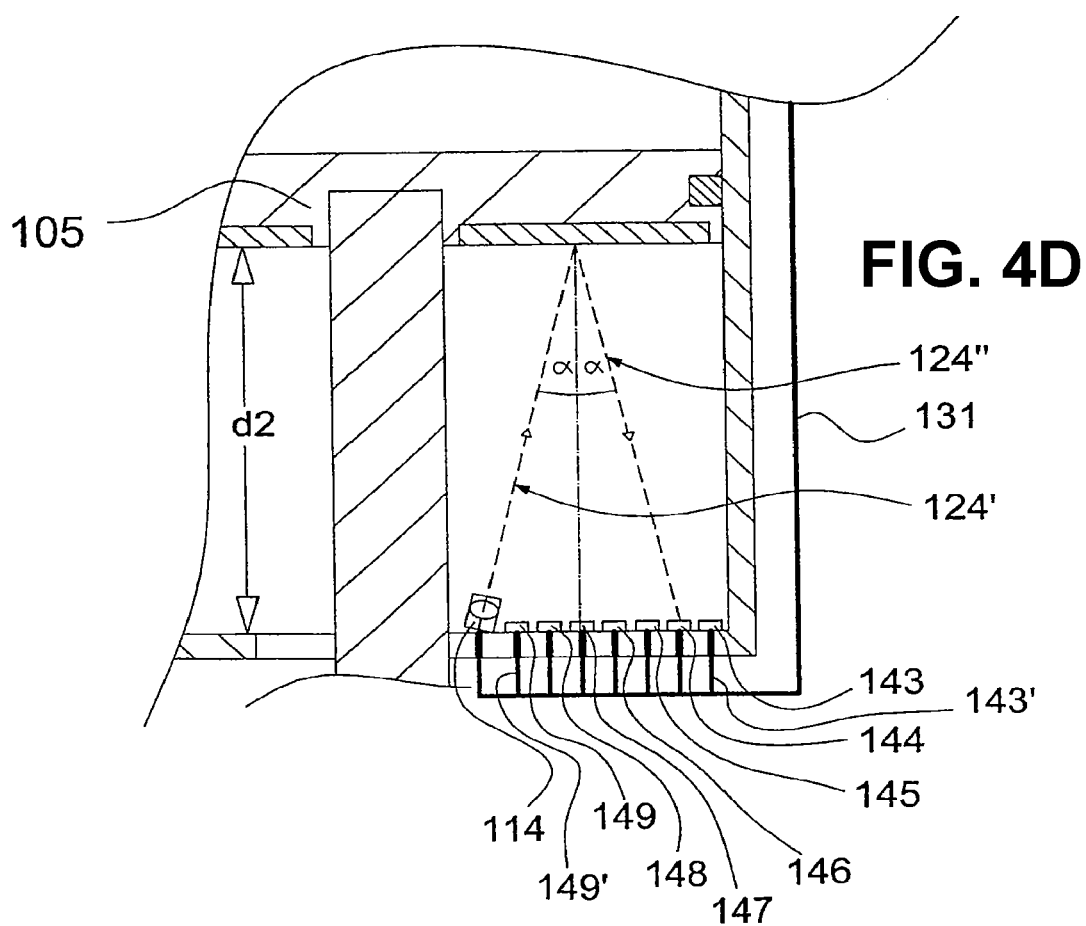

For reasons of simplicity and to better illustrate the principles of the invention the apparatus the invention shown in FIGS. 1 to 2H has been simplified in respect to commercially available apparatus of this kind in regard of ancillary features. Thus, the upward movement of the piston 5/plunger 6/rod 7 assembly of this embodiment of the apparatus of the invention is passive, that is, driven by the resilient force of the patient's chest, whereas it can be advantageously be driven by means of the compressed breathing gas used in the apparatus. In such case a substantially more complex arrangement of valves and gas lines for adducing compressed gas to compartment B and venting it from there is required. The provision of and additional pressure means for actively, that is, substantially independent of the resilient forces of a compressed chest, returning the piston to its start position does however not change the principles of the present invention, which even might be used to optimize the use of compressed gas in the displacement of the piston 5/plunger 6/rod 7 assembly in such upward (decompressing) direction.

In a second embodiment of the CPR apparatus of the invention 101 shown in FIGS. 4A to 4D the position of the piston 105 and thus the compression depth is determined by means of a source of visible light 114 and a number of photo detectors 143, 144, 145, 146, 147, 148, 149, all disposed in a radial direction, with the light source 114 innermost, on the inner face of bottom wall 103. The light source 114 is a red light photodiode whereas the photo detectors 113-119 are silicon based photodiodes operated in photoconductive mode.

The narrow and substantially parallel beam of light 124' of the photodiode 114 is directed at the lower face of the piston 114, which is provided with a ring mirror 130, at an angle .alpha. and in the same a radial direction in respect of the piston 105 axis as that of the disposition of photo detectors 113-119. The incident beam 124' is reflected at the same angle .alpha. in the direction of photo detectors 113-119 disposed on the bottom 103. The distance between the inner face of the bottom 103 and the lower face of the piston 105 provided with the mirror element 130 determines which of the photo detectors 143-149 is hit by the reflected beam 124". In a position of the piston 105 near the bottom wall 103 (distance d1, FIG. 4C) the reflected beam 124" hits the next but innermost photo detector 148, whereas in a position of the piston near the top wall 104 (distance d2, FIG. 4D) the next but outermost photo detector 144 is hit. During a downward movement of the piston 105 the reflected beam 124" thus will sweep, depending on its start position and its end position (Compression Depth position) over all or only some of the photo detectors in a radially inward direction. The photo diode 114 and the photo detectors 143, 144, 145, 146, 147, 148, 149 are connected to a microprocessor unit 113 via separate conductors 114', 143', 144', 145', 146', 147', 148', 149', respectively, which are bundled in a cable 131. The microprocessor 113 uses the signals from the photo detectors 143-149 in a time frame to control gas flow in the apparatus 100 by a solenoid valve 111 operated by a solenoid control unit 112 in a manner corresponding to that described in Example 1 for the electric signals generated by the Hall-effect switches 15, 16, 17, 18, 19. In FIGS. 4A-4D reference numbers 106, 110, 120, 121 refer to a plunger 106 carrying a chest compression pad (not shown), a tube 110 for adducing compressed breathing gas, to an electrical connection 120 between the microprocessor unit 112 and the solenoid control unit 112, and to a tube 121 for venting compressed breathing gas used for displacement of the piston 105, respectively.

Figure 5:
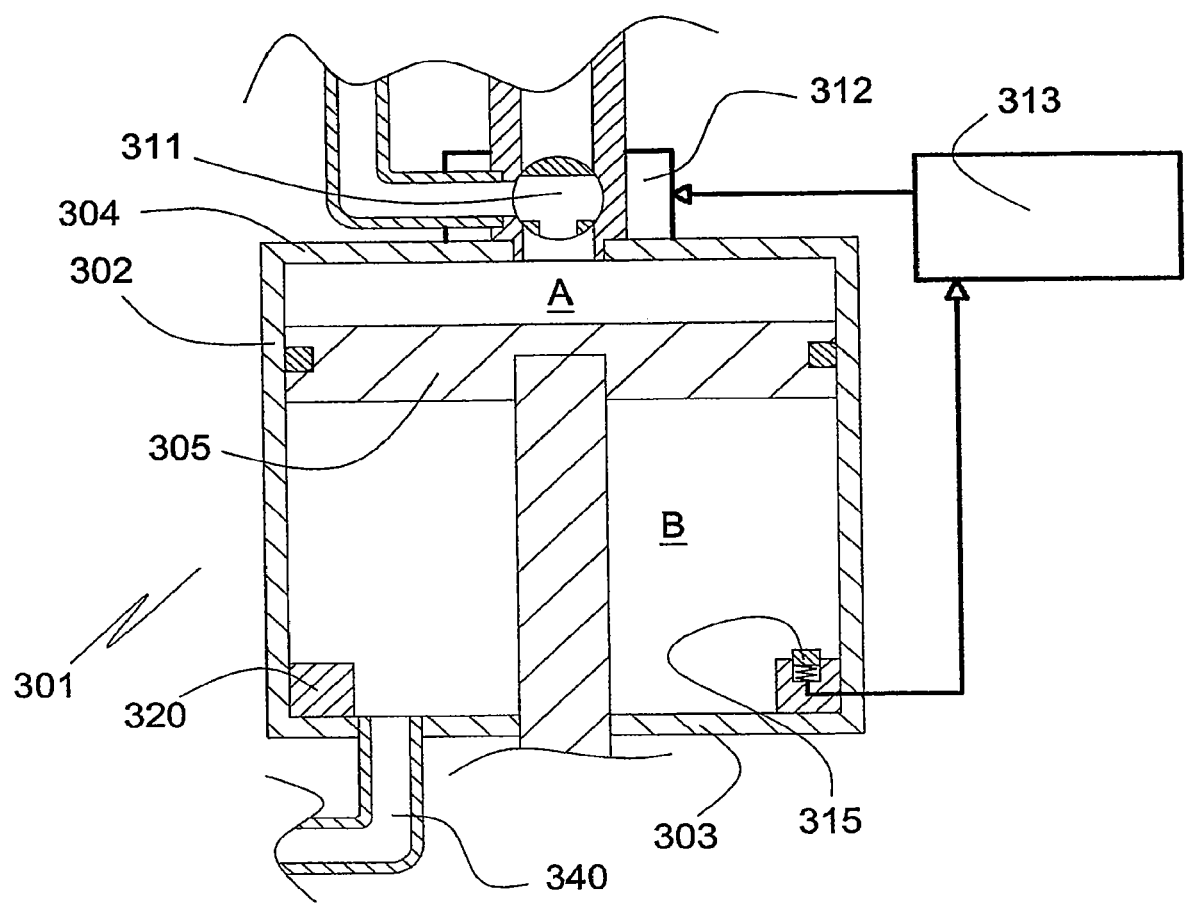
FIG. 5 shows a further embodiment of the apparatus of the invention, in the same view as in FIG. 1A.

In a third embodiment of the invention shown in FIG. 5 the stroke of the piston 305 is limited by an annular stop 320. At its lower extreme position the piston 305 hits and thereby closes a contact switch 315 of an electrical circuit comprised by a microprocessor unit 313. The microprocessor unit 313 thereby receives information about the moment at which the Compression Depth is reached. Based on this information the microprocessor's 313 issues a closing command to the control unit 312 of solenoid valve 311, in particular in a following cycle prior to the expected time of contact. In this embodiment the provision of a gas inlet tube 340 to provide driving gas to the closed lower chamber B of the cylinder housing 302, 303, 304 illustrates the principle of assisted piston 305 return that can be applied to all embodiments of the invention, if desired.

Example 2

Solenoid Valve Control Program

In the following an example of a simple main valve control program is provided (Table 1). In the example consideration is given to one Hall effect element (Hall switch), which is placed at about a desired level of piston 5/plunger 6/rod 7 assembly stop (bottom level). Time open for the decompression main valve is set to 300 ms; while this parameter is fixed in the Example, it could be controlled in precisely the same way as time open for the compression main valve.

TABLE 1

```
Initialize
set   t_open = 300           [ms]
set   adjust = true
(Parallel process #1, controls main valves)
While true do
    Is_down = false
    Main_valve_comp = true         /opens compression main valve
    Wait            t_open         /holds main valve open for t_open ms
    Main_valve_comp = false        /closes compression main valve
    Wait            300 – t_open   /wait the rest of the compression
Phase
    Main_valve_decomp = true       /opens decompression main valve
    Wait            300            /waits until whole cycle is complete
    Main_valve_decomp=false        /closes decompression main valve
    If adjust = true
        If is_down = true
                T_open = t_open – 20    /decreases t_open
        Else
                T_open = t_open+10      /increases t_open
                Adjust=false            /adjustment is now
        Complete
        End if
End while
(Parallel process #2, samples hall_element_signal input and updates variable "is_down")
while adjust = true do
            hall_effect_sample = read_digital_input_signal_of_hall_effect_element
            is_down = is_down or hall_effect_sample     /true if piston has
reached
end while                                               /hall element during
                                                        cycle
```

When the program starts the program variable (t_open), which controls the time the air supply port for the compression phase is open, is set to 300 ms, which is the maximum possible value. The apparatus then performs one cycle (compression and decompression) with this setting. During the cycle the signal from the Hall effect element is sampled. If the piston reaches the bottom of the cylinder it will be registered by the Hall effect sensor signal as a high voltage, sampled by the function "read_digital_input_signal_of_hall_effect_element" and then written to the variable is_down. is_down is the variable that indicates whether the piston has reached its bottom position during the cycle, and then determines which adjustment of t_open shall be performed. If a trigger was detected (and is_down set to true), than the variable t_open is lowered by 20 ms. This is repeated for every cycle until there is no trigger detected. During this last cycle the piston is likely to have stopped just before it reached the Hall effect element, such as a few millimetres from demand position. As is_down now is false the variable t_open is increased by 10 ms, which makes the piston move a little bit further down next cycle; this is then considered to be the final position at which the update procedure stops (since the variable adjust is set to false it cannot become true again). This setting will be used for the rest of the treatment or may be changed after some time such as, for instance, 10 minutes from start, to adapt the compression to the aforementioned change in physical properties of the chest. A block diagram of the program is shown in FIG. 3.

Example 3

Figure 6B:
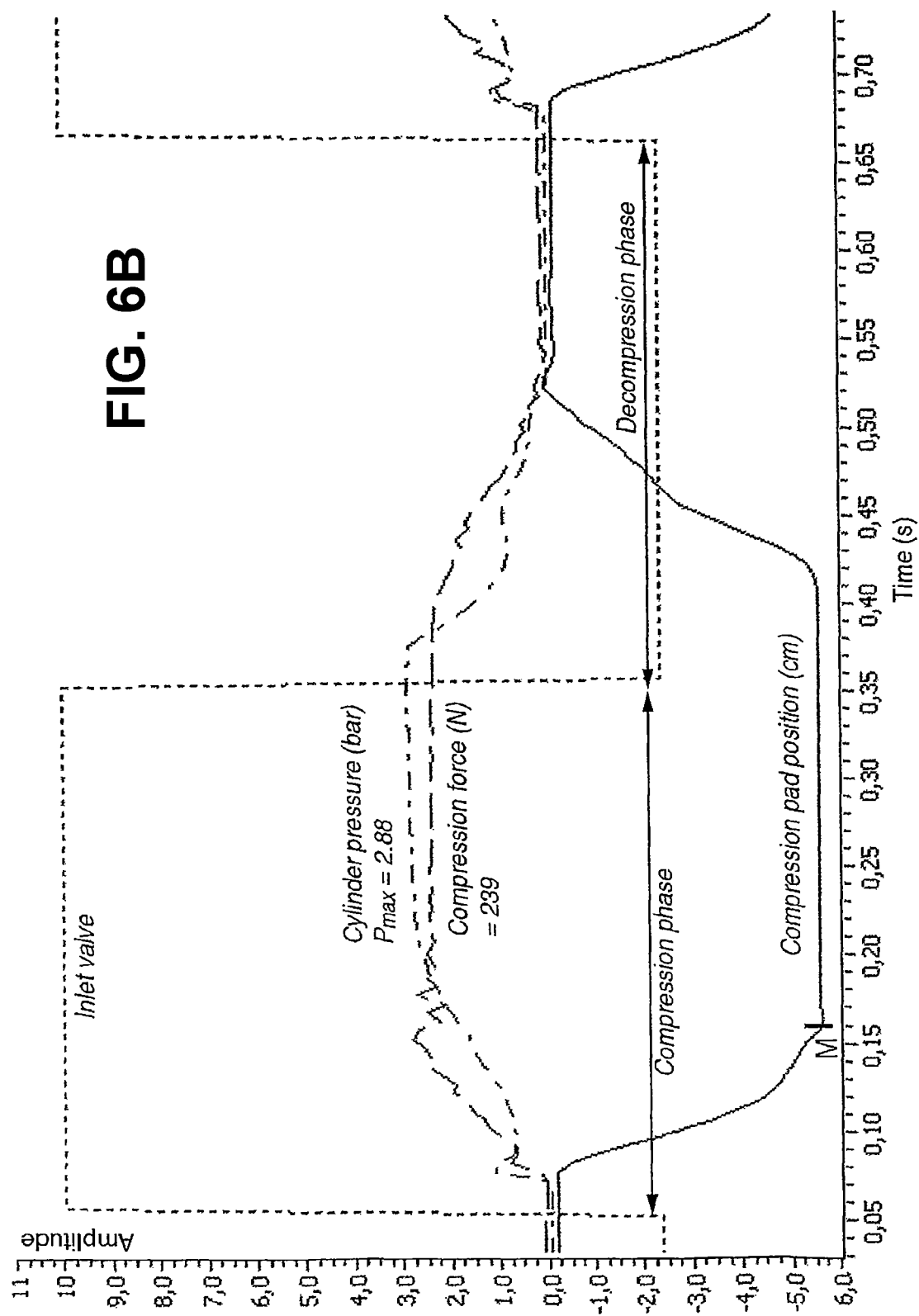
Figure 6C:
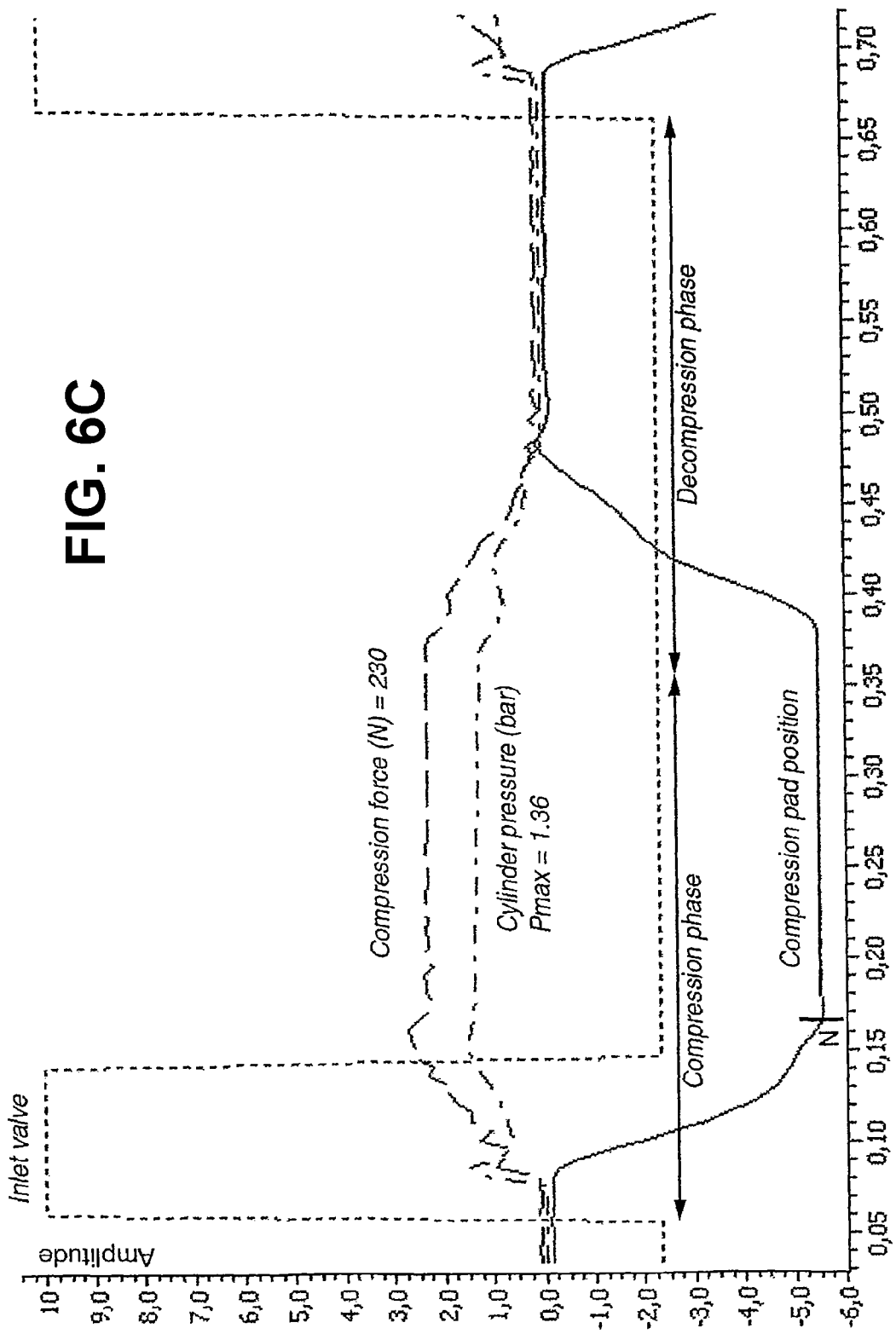

The effect of the method of the invention in the control of compressed driving gas is demonstrated by three experiments illustrated in FIGS. 6A-6C. The experiments were carried out with an air-driven reciprocating CPR device mounted on a test bench. The CPR apparatus comprises a compression cylinder 208 comprising an upper compartment 219 and a lower compartment 220 delimited in respect of each other by a piston 216 arranged displaceably in the cylinder 208. The apparatus further comprises a breast compression pad 210 attached to the piston 216 via a shaft 211, a valve control unit 212 with a valve manifold, and a gas line 213 supplying driving gas from source of compressed gas (not shown) to the compression cylinder via the valve control unit 212. The stroke (str) of the piston 216 is limited to 55 mm by means of upper 217 and lower 218 stroke limiters disposed in the upper and lower compartments, 219, 220, respectively. The gas pressure in the upper compartment 219 is measured by a manometer 214. The test bench comprises a flat base 201 on which the CPR apparatus is mounted via a pair of legs 209. The compression pad 210 abuts a top face of a sternal plate 204 resting on a support 202 via an interposed force sensor 203. The support 202 rests displaceable in a vertical direction on the base 201 via compression coil means 205, which mimic a resilient chest. A linear sliding rail 206 fixed at the base 201 allows to read the position of the sternal plate 204 and the compression pad 210 by means of a linear slide guide 207 running on the rail 206. The slide guide 207 comprises a position sensor. As indicated by reference numbers 203', 207', 212' and 214' signals from the force sensor 203, the position sensor 207, the valve control unit 212 and the manometer 214 are electrically transferred to a control unit 215 in which they are stored and from which the can be recalled and displayed. The resisting force of the compression coil means 205 against further compression at a Compression Depth of about 50 mm was set to about 500 N (FIG. 6A, 477 N) or half of that value, about 250 N (FIG. 6B, 239 N; FIG. 6C, 230 N). These and other parameter values are listed in Table 2. In all experiments the pressure of the driving gas fed to the compression cylinder was 2.91 bar.

TABLE 2

| Exp. # | Reciprocating frequ., 1/min | Max. cylinder pressure, bar | Force (N) | Compr. phase, sec | Decompr. phase, sec | Inlet valve open, sec | Compr. depth, mm |
|---|---|---|---|---|---|---|---|
| a | 98 | 2.91 | 477 | 0.31 | 0.30 | 0.31 | 52.1 |
| b | 99 | 2.88 | 239 | 0.31 | 0.30 | 0.31 | 56.0 |
| c | 99 | 1.36 | 230 | 0.30 | 0.31 | 0.09 | 55.5 |

Experiment (a), FIG. 6A, reflects the situation at the start of CPR, that is, during the first compressions administered to a patient. To provide optimal treatment it is necessary to obtain full compression, that is, a Compression Depth of about 50 mm for the average adult person, right from start and at an adequate rate of about 100 compressions per minute and even more. For this reason the minimum pressure of the driving gas is set to about 3 bar or more. This suffices to develop a compression force of about 500 (477 N in the experiment), by which the compression coil means 205 are compressed to a full stroke (str, FIG. 7), the lower stroke limiter 218 being reached at point L in FIG. 6A.

Figure 7:
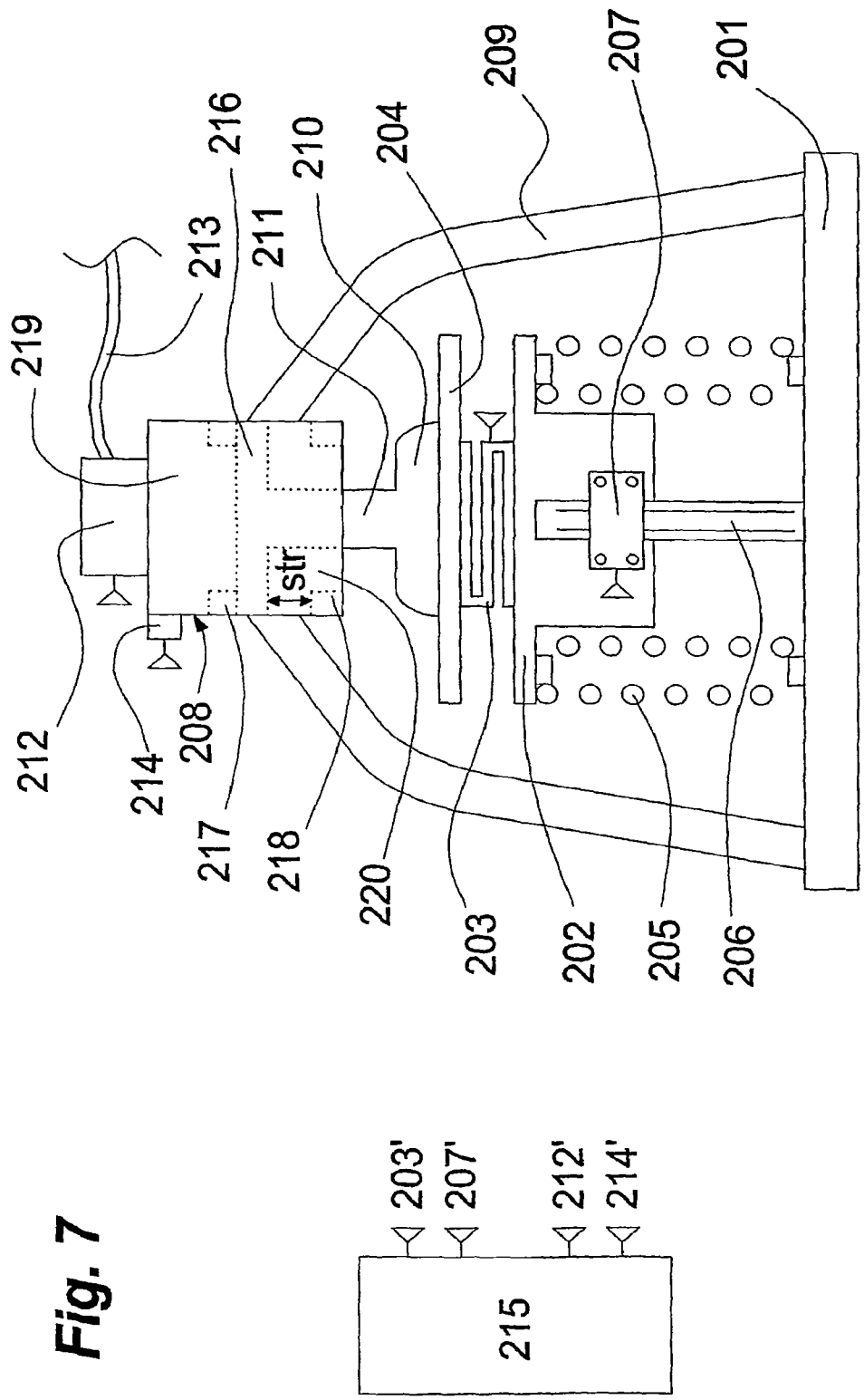
FIG. 7 is a rough sketch of the compression testing apparatus used in the experiments illustrated in FIGS. 6A-6C.

Experiment (b), FIG. 6B, reflects the situation after provision of compressions to a patient for a few minutes. During this time period the resistance of the chest diminishes by about 50%. The force of compression necessary to obtain a desired Compression Depth of about 50 mm thus is substantially reduced. In this experiment the resistance of the compression coil means 205 is set to about half (239 N) of the resistance in experiment (a). A compression profile similar to that of experiment (a) is obtained, except for the downward stroke occurring considerably faster, the lower stroke limiter 218 being reached at M. In both experiments (a) and (b) the driving gas inlet valve is open during the entire compression phase. It is closed simultaneously with the opening of the venting valve, by which the pressure in the compression chamber is released to allow the piston 216 and the compression pad 204 return to their starting position defined by upper stroke limiter 217. This return movement is supported by means of driving gas being fed to a lower chamber 219 in the housing (FIG. 7).

In experiment (c), FIG. 6C, substantially the same time v, compression pad displacement curve is obtained as in experiment (b). Experiment (c) differs from experiment (b) only in that the valve by which driving gas is adduced to the upper chamber 219 is kept open for a comparatively short time only. It is made to close at N (FIG. 7) even before the Compression Depth is reached. The final or maximum gas pressure in the compression compartment is thereby limited to about half of the pressure in experiment (b), and a corresponding saving of driving gas is obtained.

Experiments (a) to (c) demonstrate that up to 60 percent and even up to about 70 percent of driving gas can be saved by the method and the apparatus of the invention. This has been confirmed in in-vivo experiments in a pig model.

What is claimed is:

1. A mechanical cardio-pulmonary resuscitation (CPR) apparatus, comprising:
   a plunger;
   a sensor configured to sense plunger displacement information for a first reciprocating cycle, the sensor including a light source and a number of photodetectors; and
   a microprocessor configured to receive the sensed plunger displacement information and to generate plunger driving instructions for the plunger to administer a set of reciprocating cycles based at least in part on the sensed plunger displacement of the first reciprocating cycle.

2. The mechanical CPR apparatus of claim 1, wherein the generated plunger driving instructions includes a plunger displacement.

3. The mechanical CPR apparatus of claim 1, wherein the generated plunger driving instructions includes a plunger driving force.

4. The mechanical CPR apparatus of claim 1, wherein the plunger is mechanically-controlled.

5. The mechanical CPR apparatus of claim 1, wherein the first reciprocating cycle is an initial reciprocating cycle administered at an initiation of CPR treatment and the set of reciprocating cycles is a subsequent set of reciprocating cycles timed after the initial reciprocating cycle.

6. The mechanical CPR apparatus of claim 5, wherein the initial reciprocating cycle includes multiple reciprocating cycles.

7. The mechanical CPR apparatus of claim 1, further comprising a memory configured to store the sensed plunger displacement information.

8. A mechanical cardio-pulmonary resuscitation (CPR) apparatus, comprising:
   a plunger;
   a plunger displacement sensor configured to sense plunger displacement during a first reciprocating cycle, the plunger displacement sensor including a light source and a number of photodetectors; and
   a microprocessor configured to:
      receive the sensed plunger displacement from the plunger displacement sensor;
      sample the received plunger displacement for positional data of the plunger over the first reciprocating cycle; and
      generate plunger driving instructions for the plunger to administer a second reciprocating cycle based at least in part on the position data of the plunger over the first reciprocating cycle, the plunger driving instructions including instructions to actively retract the plunger.

9. The mechanical CPR apparatus of claim 8, wherein the plunger displacement sensor is configured to sense plunger displacement during a first plurality of reciprocating cycles and the microprocessor is further configured to sample the received plunger displacement over the first plurality of reciprocating cycles to determine position data of the plunger.

10. The mechanical CPR apparatus of claim 8, wherein the generated plunger driving instructions includes a plunger displacement amplitude.

11. The mechanical CPR apparatus of claim 8, wherein the generated plunger driving instructions includes a plunger driving force.

12. The mechanical CPR apparatus of claim 8, wherein the plunger is mechanically-controlled.

13. The mechanical CPR apparatus of claim 8, wherein the first reciprocating cycle is an initial reciprocating cycle administered at an initiation of CPR treatment and the second reciprocating cycle is a subsequent reciprocating cycle timed after the initial reciprocating cycle.

14. The mechanical CPR apparatus of claim 13, wherein the initial reciprocating cycle includes multiple reciprocating cycles.

15. The mechanical CPR apparatus of claim 8, further comprising a memory configured to store the sensed plunger displacement information.

16. A method for generating driving instructions for a plunger, comprising:
    sensing, with a light source and a number of photodetectors, a displacement of a plunger for a first reciprocating cycle;
    generating plunger driving instructions based on the displacement of the plunger for the first reciprocating cycle; and
    driving the plunger based on the plunger driving instructions for a second reciprocating cycle.

17. The method of claim 16, wherein the generated plunger driving instructions includes a plunger displacement distance.

18. The method of claim 16, wherein the first reciprocating cycle is an initial reciprocating cycle administered at an initiation of CPR treatment.

* * * * *